(12) United States Patent     (10) Patent No.: US 8,307,823 B2
Schmal     (45) Date of Patent: Nov. 13, 2012

(54) BREATHING AID

(76) Inventor: William Schmal, Chicago Heights, IL (US)

( * ) Notice: Subject to any disclaimer, the term of this patent is extended or adjusted under 35 U.S.C. 154(b) by 325 days.

(21) Appl. No.: 12/653,813

(22) Filed: Dec. 21, 2009

(65) Prior Publication Data

US 2011/0146672 A1     Jun. 23, 2011

(51) Int. Cl.
*A61M 16/00* (2006.01)

(52) U.S. Cl. .................................. 128/200.24; 602/902

(58) Field of Classification Search ............. 128/200.24, 128/206.29, 848; 602/902
See application file for complete search history.

(56) References Cited

U.S. PATENT DOCUMENTS

| 5,533,523 A * | 7/1996 | Bass et al. ...................... 128/859 |
| 6,976,491 B2 * | 12/2005 | D'Agosto ...................... 128/859 |
| 2004/0211430 A1 * | 10/2004 | Pivovarov ...................... 128/848 |

* cited by examiner

*Primary Examiner* — Quynh-Nhu H Vu
(74) *Attorney, Agent, or Firm* — Wood, Phillips, Katz, Clark & Mortimer

(57) ABSTRACT

In accordance with the principles of the present invention, breathing aid is provided. The breathing aid includes a middle portion that defines a breathing aperture that provides air flow out of the mouth of the user. An incisor is defined on the top of the middle portion and sized to receive the upper incisors teeth of the user. The location of the incisor aperture along the middle portion providing proper placement of the breathing aid in the user's mouth. An inside end of the middle portion is provided at an angle. A pair of wing-like protrusions extend sideward from the middle portion, the protrusions sized to extend outwardly beyond the sides of a user's mouth in order to prevent the breathing aid from entering the mouth.

19 Claims, 2 Drawing Sheets

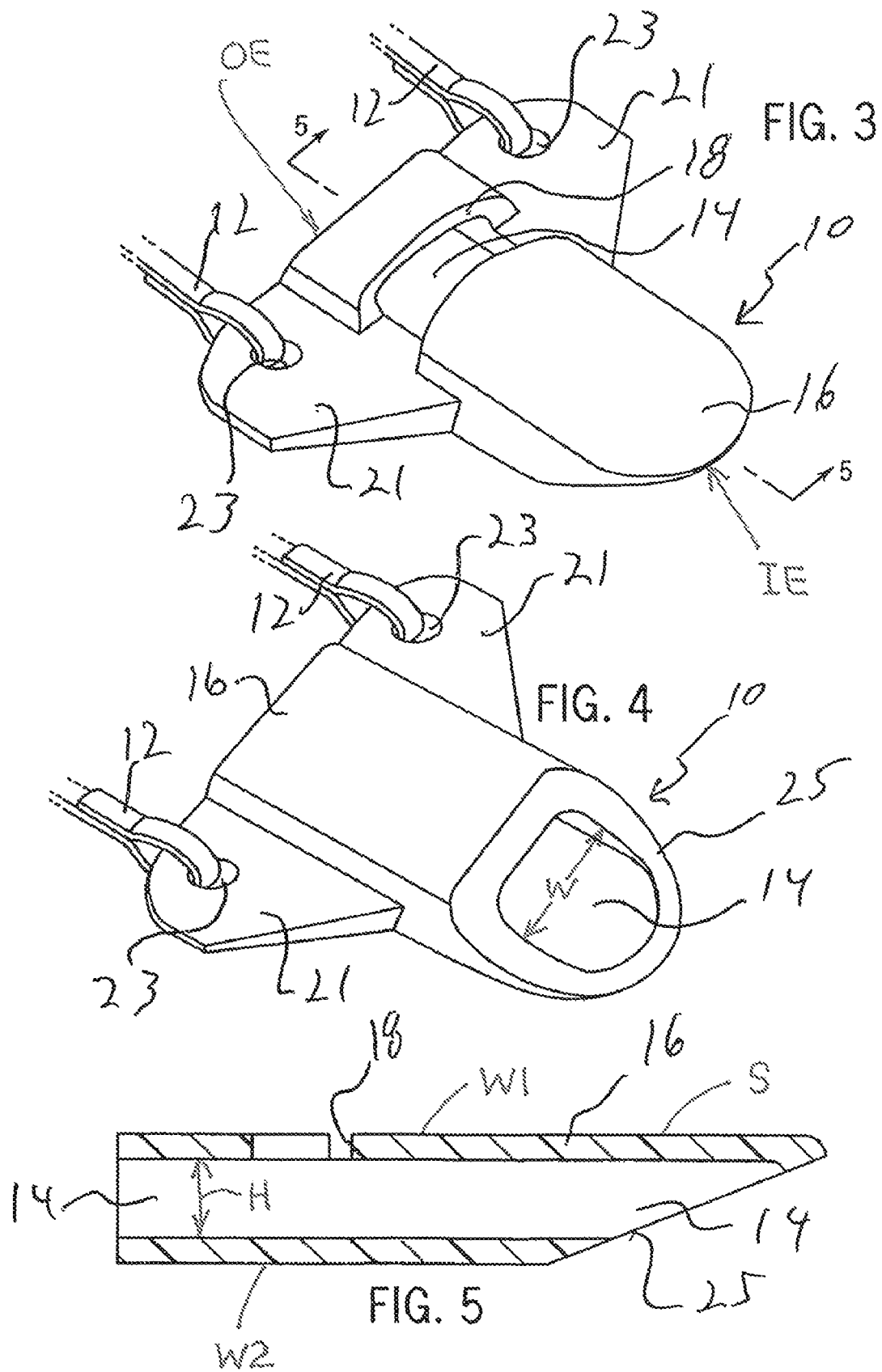

BREATHING AID

FIELD OF THE INVENTION

The present invention relates to aids in breathing.

BACKGROUND OF THE INVENTION

Breathing exercises help people relax, because breathing exercises make the body feel like it does when it is already relaxed. Deep breathing is one of the best ways to lower stress in the body. This is because when breathing deeply the body sends a message to the brain to calm down and relax. The brain in turn sends this message to the body. Things that happen when stressed, such as increased heart rate, fast breathing, and high blood pressure, all decrease when breathing deeply to relax.

The idea behind relaxation breathing is that the brain has received inaccurate information in its "suffocation monitor" and it signals back a warning that begins a process of hyperventilation. The effect is an attempt to keep breathing in life-threatening situations. Once the level of $CO_2$, which seems to trigger this alarm, is stabilized, breathing returns to normal. So relaxation breathing is a means of changing this $CO_2$ level.

Breathe affects the whole body. Full, deep breathing is a good way to reduce tension, feel relaxed, and reduce stress. When relaxed, breathing tends to be slow and gentle. Breathing can be shallow or deep; one of the ways breathing exercises help relax is getting a person to feel the way they do when they are already relaxed.

There are different ways to breathe to relax. When stressed, breathing exercises have health benefits such as lowering blood pressure, slowing a fast heart rate, reducing sweat, and helping with digestion. Murray M T, Pizzorno J E Jr. Stress management. In J E Pizzorno Jr, M T Murray, eds., *Textbook of Natural Medicine,* 3rd ed., vol. 1, pp. 701-708. St. Louis: Churchill Livingstone (2006); see also Payne R *Relaxation Techniques: A Practical Handbook for the Health Care Professional,* 3rd ed. Edinburgh: Churchill Livingstone (2005). Breathing exercises can be done whenever and wherever. Breathing exercises do not take long to do and do not require costly expenditures such as for example joining a gym.

There are lots of breathing exercises that can help relax. For example, belly breathing is simple to learn and easy to do. One simply sits in a comfortable position. One hand is placed on the belly just below your ribs and the other hand on the chest. A deep breath is taken in through the nose, and the belly pushes the hand out. The chest should not move. Breathe out through pursed lips. Feel the hand on the belly go in, and use it to push all the air out. Do this breathing 3 to 10 times.

A related breathing exercise is the 4-7-8 breathing exercise. This can be done either sitting or lying down. To start, put one hand on the belly and the other on the chest as in the belly breathing exercise. A deep, slow breath is taken from the belly, and when breathing in silently count to four. With breath held, silently count from one to seven. Breathe out completely and silently count from one to eight. Try to get all the air out of the lungs by the time eight is achieved. Repeat 3 to 7 times 1 m.

A more advanced breathing exercise is roll breathing. The object of roll breathing is to develop full use of the lungs and to focus on the rhythm of breathing. Put the left hand on the belly and the right hand on the chest. Notice how the hands move as breathing occurs. Practice filling the lower lungs by breathing so that the belly (left) hand goes up during inhale and the chest (right) hand remains still. Always breathe in through the nose and breathe out through the mouth. Do this 8 to 10 times.

When the lower lungs have filled and emptied 8 to 10 times, a second step is added to the breathing: inhale first into the lower lungs as before, and then continue inhaling into the upper chest. The right hand will rise and the left hand will fall a little as the belly falls. Exhale slowly through the mouth, as first the left hand and then the right hand fall. During exhale, tension leaves the body. Practice breathing in and out in this way for 3 to 5 minutes. Notice that the movement of the belly and chest rises and falls like the motion of rolling waves.

A breathing exercise to use first thing in the morning to relieve muscle stiffness and clear clogged breathing passages is morning breathing. From a standing position, bend forward from the waist with the knees slightly bent, letting the arms dangle close to the floor. Inhale slowly and deeply, while returning to a standing position by rolling up slowing, lifting the head last. Hold the breath for just a few seconds in this standing position. Exhale slowly while returning to the original position, bending forward from the waist.

A more spontaneous breathing exercise can help wherever stress levels soar. This exercise in breathing can be done for as little as 3 to 5 minutes at a time. Sit upright in a comfortable position. Focus on present state and existence (this is often termed being "mindful"). Block out intrusive thoughts. Close the eyes. Pay attention to breathing. Inhale slowly through the nose, taking several seconds. Exhale through the mouth, trying to make the exhalation phase last twice as long as the inhalation. Continue this mindful breathing for 3 to 5 minutes.

A well know breathing technique used in childbirth is the Lamaze Technique. Developed in the 1940s by French obstetrician Dr. Fernand Lamaze as an alternative to the use of medical intervention during childbirth, Dr. Lamaze was influenced by Soviet childbirth practices, which involved breathing and relaxation techniques under the supervision of a "monitrice" or midwife. Lamaze breathing techniques teach a pattern of breathing to decrease the feeling of pain. As each contraction begins a deep or "cleansing" breath is taken. This deep breath is followed by slow, deep breathing in through the nose and out through pursed lips. The focus on careful breathing distracts and decreases perception of discomfort. If the urge to push is felt before the cervix is fully dilated, more rapid, short breaths are recommended.

What all these breathing techniques share is the importance of inhaling through the nose and exhaling through a properly positioned mouth; indeed, particularly with newcomers (as most newly expectant mothers are, for example), concentrating on the proper mouth position detracts from the relaxation. It is only with a great deal of practice that one comes to the properly positioned mouth unconsciously; again, for example, a newly expectant mother may not achieve this level of practice, particularly when called upon to perform breathing techniques during the stress of birth. What would thus be useful would be an aid in breathing techniques.

SUMMARY OF THE INVENTION

The present invention provides an aid in breathing techniques in general and in particular to properly positioning a user's mouth. In accordance with the principles of the present invention, a breathing aid is provided. The breathing aid includes a middle portion that defines a breathing aperture that provides air flow out of the mouth of the user. An incisor aperture is defined on the top of the middle portion and sized to receive the upper incisors teeth of the user. The location of the incisor aperture along the middle portion providing proper placement of the breathing aid in the user's mouth. An inside end of the middle portion is provided at an angle. A pair of wing-like protrusions extends sideward from the middle portion, the protrusions sized to extend outwardly beyond the sides of a user's mouth in order to prevent the breathing aid from entering the mouth.

BRIEF DESCRIPTION OF THE DRAWINGS

FIG. 3 is a top view of a breathing aid in accordance with the principles of the present invention.

FIG. 4 is a bottom view of a breathing aid in accordance with the principles of the present invention.

FIG. 5 is a cross-sectional view of a breathing aid in accordance with the principles of the present invention.

DETAILED DESCRIPTION OF A PREFERRED EMBODIMENT

Figure 1:
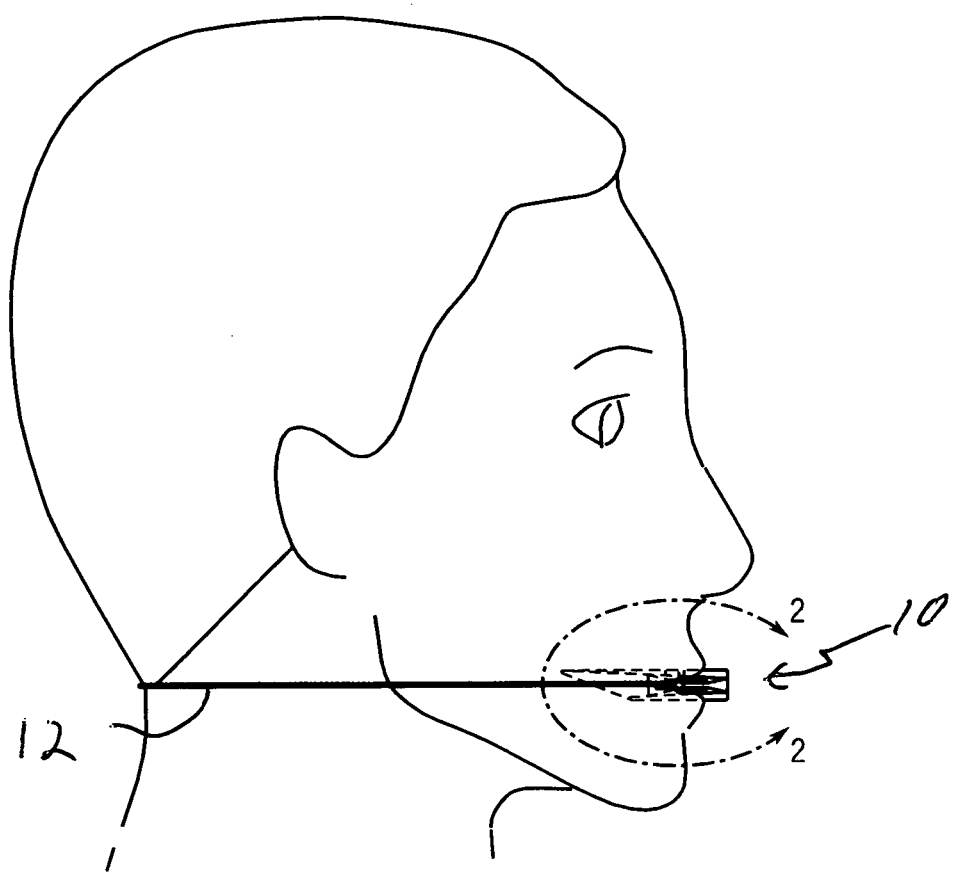
FIG. 1 is an elevated view of a breathing aid in accordance with the principles of the present invention in use in a user's mouth.

In accordance with the principles of the present invention, a breathing aid is provided that aids in the use of breathing techniques to aid in relaxation. Referring to FIG. 1, an elevated view of a breathing aid 10 in accordance with the principles of the present invention in use in a user's mouth is seen. The breathing aid 10 can include an elastomeric strap 12 that can be secured about the user's head to secure the breathing aid 10 around user's neck, making the breathing aid 10 available 24/7 whenever and wherever needed.

Figure 2:
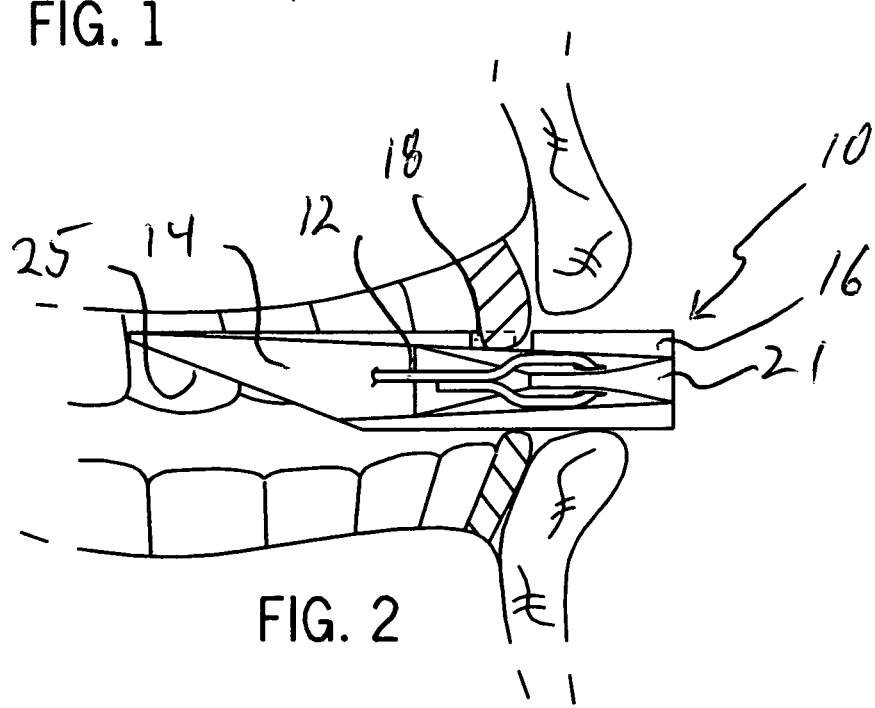
FIG. 2 is a detailed view of the breathing aid of FIG. 1, with the user's mouth partially cut-away.

Referring to FIG. 2, a detailed view of the breathing aid 10 of FIG. 1, with the user's mouth partially cut-away is seen. The breathing aid 10 defines a breathing aperture 14 that provides an unobstructed air flow out of the mouth of the user, as detailed below. The breathing aid 10 can be preferable made of a malleable inert material such as for example silicon that provides sufficient firmness to operate effectively to maintain the breathing aperture 14 that provides an unobstructed air flow out of the mouth of the user while providing for a comfortable fit.

Referring to FIG. 3, a top view of a breathing aid 10 in accordance with the principles of the present invention is seen. The breathing aid 10 includes a middle portion 16 through which the breathing aperture 14 that provides an unobstructed air flow out of the mouth of the user is defined.

The middle portion 16 has an inside end IE and an outside end OE. The breathing aperture 14 is bounded by vertically spaced walls W1, W2 that are straight and substantially parallel to each other over a majority of an extent of the middle portion 16 between the inside and outside ends IE, OE. The breathing aperture 14 has an area with a height H and a width. W that is substantially greater than the height. The area of the breathing aperture 14 is substantially constant over the extent where the walls W1, W2 are substantially straight and parallel.

Defined on the top wall W1 of the middle portion 16 is an incisor aperture 18 sized to receive the upper incisors teeth on one jaw bone of the user, as seen in FIG. 2. In addition, the location of the incisor aperture 18 along the length of the middle portion 16 provides the proper placement of the breathing aid 10 and the breathing aperture 14 in the user's mouth. The aperture 18 extends through an exposed surface S on one of the walls W1.

Extending sideward from the middle portion 16 are a pair of wing-like protrusions 21. The wing-like protrusions 21 are sized to extend outwardly beyond the sides of a user's mouth in order to prevent the breathing aid 10 from entering the mouth. In addition, the elastomeric strap 12 can be secured to the wing-like protrusions 21 in order to keep the elastomeric strap 12 away from the mouth. Thus, strap apertures 23 through which the elastomeric strap 12 can be secured are located a sufficient distant from the middle portion 16 such that the elastomeric strap 12 is unlikely to accidentally enter the user's mouth.

Referring to FIG. 4, a bottom view of a breathing aid 10 in accordance with the principles of the present invention is seen. Again, the breathing aid 10 includes the middle portion 16 through which the breathing aperture 14 that provides an unobstructed air flow out of the mouth of the user is defined. The inside end 25 of the middle portion 16 is provided at an angle in order to increase the exposed area of the breathing aperture 14 within the user's mouth. This can be seen in detail in FIG. 5, which shows a cross-sectional view of a breathing aid 10 in accordance with the principles of the present invention, and in FIG. 2.

Thus referring back to FIG. 2, with the upper incisors teeth properly placed in the incisor aperture 18 and closing jaw, the lower incisors teeth press firmly against the bottom of the breathing aid 10 slightly behind the upper incisors teeth, which presses the breathing aid 10 tightly in the mouth of the user while the lips rest on the wing-like protrusions 21.

A non-limiting example of an exemplary breathing aid in accordance with the principles of the present invention follows. This exemplary breathing aid can have a width from the ends of the wing-like protrusions 21 of 2½ inches. The width of the wing-like protrusions 21 at the base where they meet the middle portion 16 can be 1 inch. The height of the wing-like protrusions 21 at the base can be 3/16 inch.

This exemplary breathing aid can have a length of 2½ inches. The width of the middle portion 16 can be 1 inch and the height can be ⅜ inch. The breathing aperture 14 can be 3/16 inch. The incisor aperture 18 can be ¼ inch in width and can be located ½ inch from the winged-end of the middle portion 16, as measured at the edge of the middle portion 16. The angled inside end 25 of the middle portion 16 can be ¾ inch in length.

Thus, the present invention provides an aid in breathing techniques in general and in particular to properly positioning a user's mouth. While the present invention is particularly useful in the Lamaze Technique during childbirth, it can be used in an endless variety if situations to help in relaxation. For example, by using the present invention on a cold winter day a user can actually warm up their very cold hands and increase warm blood circulation in a reasonable amount of time. For example, after waiting in cold weather for your train to arrive, a user enters the train and sits down. The present invention is placed in the user's mouth. One end of a newspaper can be placed on your lap and the other end under your nose. The user's cold hands can be placed under the newspaper while moving your fingers, breath in your nose and exhale through my invention. The warmth from your breath will be directed towards your hands and chest, warming you quicker. If you are at a football game and your hands are very cold, place the present invention into your mouth, hold a blanket under your nose, and breath in your nose and out through my invention. Again, the warmth from your breath will be directed to your cold hands, warming you quicker.

While the invention has been described with specific embodiments, other alternatives, modifications, and variations will be apparent to those skilled in the art. Accordingly, it will be intended to include all such alternatives, modifications and variations set forth within the spirit and scope of the appended claims.

What is claimed is:

1. A breathing aid for a user, the breathing aid comprising:
   a middle portion having an inside end and an outside end and defining a breathing aperture that provides air flow out of the mouth of the user between the inside and outside ends,
   the middle portion having an exposed surface that extends in a substantially straight line over a length between the inside and outside ends,
   the breathing aperture having a height and a width, that is substantially greater than the height, between the inside and outside ends of the middle portion,
   the height and width of the breathing aperture substantially constant over a majority of an extent of the middle portion between the inside and outside ends,
   the inside end of the middle portion having an exposed area of the breathing aperture that is greater than an exposed area of the breathing aperture at the outside end;
   an incisor aperture defined through the exposed surface of the middle portion and sized to receive a user's incisors teeth on one of the user's law bones, the location of the incisor aperture along the middle portion providing proper placement of the breathing aide in the user's mouth; and
   a pair of protrusions extending oppositely sideward from the middle portion.

2. The breathing aid of claim 1 further comprising an elastomeric strap secured to the protrusions to hang the breathing aid around the neck of a user.

3. The breathing aid of claim 1 further being comprised of a malleable inert material.

4. The breathing aid of claim 3 further wherein the malleable inert material is silicon.

5. The breathing aid of claim 1 further wherein the protrusions are wing-like.

6. The breathing aid of claim 1 further wherein the inside of the middle portion is formed at an angle to define the exposed area at the inside end.

7. The breathing aid of claim 6 further wherein the angled inside end of the middle portion is ¾ inch in length.

8. The breathing aid of claim 1 further wherein a width of the breathing aid from ends of the protrusions is 2½ inches.

9. The breathing aid of claim 1 further wherein a length of the breathing aid is 2½ inches between the inside and outside ends.

10. The breathing aid of claim 1 further wherein a width of the middle portion is 1 inch and a height is ⅜ inch.

11. The breathing aid of claim 1 further wherein the breathing aperture has a height of 3/16 inch.

12. The breathing aid of claim 1 further wherein the incisor aperture is ¼ inch in width and is located ½ inch from the winged-end of the middle portion, as measured at an edge of the middle portion.

13. A breathing aid for a user, the breathing aid comprising:
    a middle portion having an inside end and an outside end and defining a breathing aperture that provides air flow out of the mouth of the user between the inside and outside ends,
    the breathing aperture bounded by vertically spaced walls that are straight and substantially parallel to each other over a majority of an extent of the middle portion between the inside and outside ends,
    the breathing aperture having a substantially constant area over an extent where the walls are straight and parallel, the constant area having a height and a width that is substantially greater than the height,
    an incisor aperture defined on one of the walls of the middle portion where the one of the walls is straight to receive the incisors teeth of the user on one of the user's jaw bones, the location of the incisor aperture along the middle portion providing proper placement of the breathing aid in the user's mouth; and
    the inside end of the middle portion configured to provide an enlarged exposed area of the breathing aperture.

14. The breathing aid of claim 13 further being comprised of a malleable inert material.

15. The breathing aid of claim 14 further wherein the malleable inert material is silicon.

16. The breathing aid of claim 13 further comprising a pair of protrusions extending sideward from the middle portion, the protrusions sized to extend outwardly beyond the sides of a user's mouth in order to block the breathing aid from entering the mouth.

17. The breathing aid of claim 16 further wherein the protrusions are wing-like.

18. The breathing aid of claim 16 further comprising an elastomeric strap secured to the protrusions to hang the breathing aid around the neck of a user.

19. The breathing aid of claim 13 wherein the inside end of the middle portion is provided at an angle to provide the enlarged exposed area of the breathing aperture.

* * * * *